United States Patent [19]

Adrian

[11] 4,228,352
[45] Oct. 14, 1980

[54] APPARATUS FOR MEASURING THE CONCENTRATION OF GASES

[76] Inventor: Werner Adrian, Im Roth 19, D-7505 Ettlingen-Oberweier, Fed. Rep. of Germany

[21] Appl. No.: 11,718

[22] Filed: Feb. 12, 1979

[30] Foreign Application Priority Data

Feb. 13, 1978 [DE] Fed. Rep. of Germany ....... 2805972

[51] Int. Cl.³ .................... G01J 1/00; G01N 21/00
[52] U.S. Cl. ................................ 250/343; 356/440
[58] Field of Search ............ 250/343, 373; 356/436, 356/440; 128/2 C

[56] References Cited

U.S. PATENT DOCUMENTS

| | | | |
|---|---|---|---|
| 2,212,211 | 8/1940 | Pfund | 250/343 |
| 3,319,071 | 5/1967 | Werth et al. | 250/339 |
| 3,792,272 | 2/1974 | Harte et al. | 250/343 |
| 3,997,786 | 12/1976 | Lauer et al. | 250/343 |

*Primary Examiner*—Davis L. Willis
*Assistant Examiner*—Janice A. Howell
*Attorney, Agent, or Firm*—Colton & Stone, Inc.

[57] ABSTRACT

A tubular measuring chamber (3) is described for temporarily holding alveolar breath for determining the quantity of alcohol in the breath of infra red radiation absorption. The radiation path length between an I.R. source (1, 2) and a condenser lens (7) and detector (8) is made a multiple of the actual length of the tube by bending the tube in any convenient way e.g. a helix (FIG. 1 and FIG. 3), a serpentine (FIG. 2), or meanderingly with definite bends (FIGS. 4–7).

The internal surface of the tube (3) is made highly reflective to I.R. and plane reflectors (10) are located at definite bends in the tube or between different sections of tube (see FIGS. 4–7), to deflect radiation from one tube section to the next.

A saliva trap and mouthpiece (6) to receive the breath is connected mid-way along the tube (3) between the radiation source (1, 2) and condenser (7).

6 Claims, 7 Drawing Figures

APPARATUS FOR MEASURING THE CONCENTRATION OF GASES

DESCRIPTION

Field of Invention

The invention relates to apparatus for measuring the concentration of gases by radiation absorption, in particular the concentration of alcohol vapour in alveolar breath.

Background to the Invention

In known apparatus for measuring the concentration of a gas by radiation absorption at characteristic absorption bands for the gas, the gas to be analysed is introduced into a measuring chamber. This is exposed to radiation of the specific wavelength. The radiation flux is reduced by gas molecules which absorb the radiation at that specific wavelength and if the flux of the radiation entering the chamber is $\phi_o$, the flux as it leaves the measuring chamber will be $\phi$.

The relationship between $\phi$ and $\phi_o$ is given by the Lambert-Beer law:

$$\phi = \phi_o e^{-mlc}$$

Here, m is a material constant, l is the length of the radiation path through the absorbing gas and c is the concentration of the absorbing gas in the measuring chamber. If it is necessary that a very low gas concentration will produce a given $\phi = \phi_o$ ratio, then the path length of the radiation l must be increased. The resolution of the detectors and the amplifier connected to the outlet side also determines the sensitivity.

In known apparatus for gas analysis with the aid of spectrophotometers, measuring chambers are used in which the radiation path is deflected via an optical system. For example, a principle given by White allows wavelengths up to 10 m to be produced. However, the apertures are narrow and the chamber volume amounts to more than six liters. Such as arrangement is however quite unsuitable for measuring the concentration of alcohol molecules in breath. To achieve this measurement the chamber must be filled only with alveolar respiratory air and consequently the measuring chamber must have an extremely small volume. For this reason the volume of a measuring chamber for measuring alcohol concentrations in alveolar breath should not exceed about 100 cc.

Prior Art

Apparatus is known in which a hollow sphere with highly reflective inner walls forms the measuring chamber. However, this arrangement is completely unsuitable for measuring the concentration of alcohol in breath, as a sphere has the greatest volume for a given surface area and this is exactly the opposite of what is required. Secondly, multiple reflections within the ball means that there is no single well defined path length and the chamber will not therefore be tuned to any particular path length. Deflection of several components, more or less reduced by the alcohol level is obtained (U.S. Pat. No. 3,319,071).

Another known measuring chamber is in the form of a hollow cylinder. The image of a radiation source is projected through an opening in one end of the cylinder, and is reflected by both end surfaces. This gives a radiation path which exceeds the length of the cylinder. However, this known measuring chamber has a relatively large volume (U.S. Pat. No. 2,212,211). A measuring chamber with such a large volume cannot be used for measuring the concentration of alcohol in breath, since with such a large volume it cannot be guaranteed that it will be filled exclusively with alveolar breath, i.e. air originating directly from the lung vesicles of the subject under test.

Infra red radiation elements with parabolic or elliptical reflecting profiles are also known, for melting, welding, drying, etc. With an elliptical shape, a focal line is produced at a distance from the reflector, say 16 mm. If the reflector is gold-plated, IR radiation will be concentrated in this focal line (G-I-T Laboratory Technical Journal, Vol. 13, No. 4 (1969) p. 353).

The object of an invention described and claimed in a previous application filed by the Applicant, Ser. No. 805,334 now U.S. Pat. No. 4,190,363, was to produce apparatus with a measuring chamber which had an exceptionally small volume with a well defined long radiation path and a large aperture. The solution to this problem as represented by the invention in the preceding application involved the use of a measuring chamber made from a tube coiled into a helix having at least one turn. Due to multiple reflection on the optically-effective inner surface of the tube, the radiation path through the measuring chamber, which corresponds to the path length for radiation through the medium to be measured, was extended. The effective radiation path length was thus increased to a multiple of the path length dictated by the geometrical longitudinal dimensions of the measuring chamber.

A conventional ellipsoid lamp, vacuum-coated with gold and with a quartz-halogen light source, was used as the radiation source. The beams were united in the second focal point of the ellipsoid. Due to the extent of the filament and inaccuracies in the surface of the ellipsoid reflector, a focal area of about 6 mm diameter was obtained. For the intended application, this was sufficiently punctiform. This focal area was projected at the radiation inlet into the measuring chamber. The radiation from this entered the tube and, after reflection on the optically-effective surfaces of the inner walls, reached the radiation outlet, from where it travelled to the detector.

In practice, with a chamber volume of less than 60 cc, and a tube of 8 mm internal diameter which is bent round in a helix with a radius of curvature of about 15 cm, and which has a total length of only 95 cm, an effective wavelength of more than 2.5 m can be obtained due to multiple reflection on the inner walls.

A tube was used for the measuring chamber which has particularly high gloss reflecting inner walls. The tube was coiled one or several times. Depending on the particular lining material used, reflection or total reflection occurred on the inner wall of the tube. Radiation entering the tube at the inlet, left the tube at the radiation outlet after having been reflected many times on the inner tube wall. At the outlet a condenser lens could be situated (transparent at the operating wavelength) which focuses the radiation onto the surface of the detector. In this way, a large effective path length was obtained with a good effective level yet with a small chamber volume. The radiation entering into the tube was found to be reduced by only small losses during reflection.

The Invention

According to the present invention in apparatus for measuring the concentration of gases by radiation absorption in a tubular measuring chamber, the effective path length of radiation through the chamber is made a multiple of the actual length of the tube, by bending the tube.

In a preferred embodiment the measuring chamber is coiled helically.

In another preferred embodiment it is coiled serpentine-fashion.

It has been found that the tube can equally well be coiled in a spiral, or meanderingly and randomly.

According to a preferred feature of the invention, where the tubular measuring chamber is coiled in a meandering or random manner and corners and bends are introduced into the path, reflecting surfaces may to advantage be arranged in the corners or bends at an angle of 45° to the general direction of the radiation around the bend. These reflectors serve to deflect the radiation along the length of the tubular measuring chamber.

Generally a coiled tubular measuring chamber can be thought of as having separate sections with bends or corners between the separate sections. In some arrangements the separate sections will all lie in one plane. According to another preferred feature of the invention, where separate sections lie in different planes, each plane preferably subtends an angle of 90° with an adjacent plane.

Although the separate sections of a tubular measuring chamber coiled in a meandering manner may be of equal length, a measuring chamber embodying the invention can equally well be formed with the separate sections of the tubing of different lengths, e.g. with shorter deflecting sections disposed between longer lengths of tubing.

According to a further development of the invention a saliva trap is connected to a centrally located section of the tubing. With this form of construction a closure at the ends of the tubular measuring chamber can be dispensed with.

The invention will now be described by way of example with reference to the accompanying drawings.

In the drawings

FIG. 1 is a schematic plan view of one embodiment of the invention in which the measuring chamber is coiled in a circle, FIG. 2 is a cross-section through another embodiment of the invention in which the measuring chamber is coiled in serpentine fashion, FIG. 3 is a schematic perspective view of an embodiment of the invention in which the tubular measuring chamber is coiled helically, FIG. 4 is a schematic perspective view of an embodiment of the invention in which the tubular measuring chamber is coiled in a meandering form, FIG. 5 is a schematic perspective view similar to FIG. 4 with a blowing-in connection in a central section of the tubing, FIG. 6 is a schematic perspective view of a convenient realisation of the embodiment of FIG. 5, with different lengths and types for the individual sections of tubing, and FIG. 7 is a schematic perspective view of an embodiment of the invention based on that shown in FIG. 5, but with the different lengths of tubing lying in different planes.

Detailed Description of the Drawings

Figure 1:
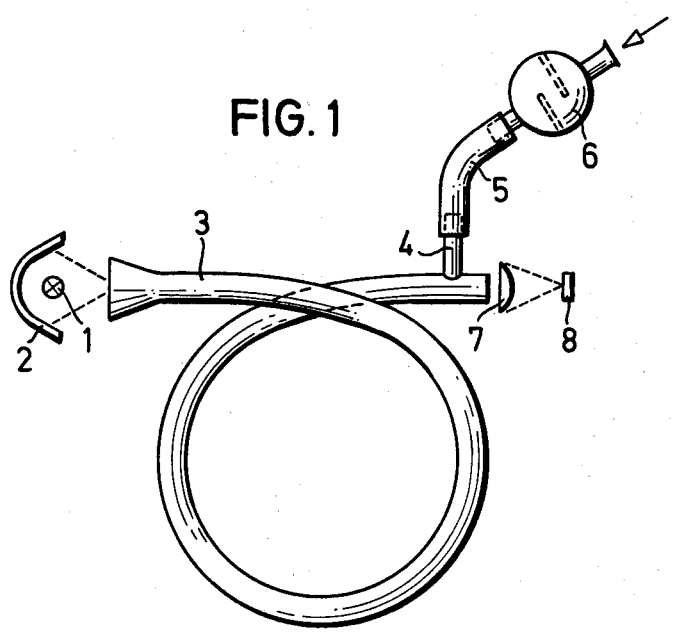

In the construction form shown in FIG. 1 there is a radiation source 1 in the focal point of an ellipsoid reflector 1. The entrance to the measuring chamber 3 widens out in the form of a trumpet and therefore also picks up dispersed radiation from the radiation source 1. The measuring chamber 3 is coiled once, helically or in a circle with an approximately constant radius of curvature. The measuring chamber 3 either has a high gloss reflecting inner surface which is effective at the operating wavelength being used, or is vacuum-coated with several layers of a material which has a refractive index n so that radiation striking it, even at an acute angle, is totally reflected.

A gas to be measured is blown in via a pipe 5 and a saliva trap 6 through a connection 4 in the vicinity of the radiation outlet from the measuring chamber 3. The measuring chamber 3 is closed at the radiation outlet by a condenser lens 7.

With this arrangement any gases or vapours already in the measuring chamber 3 are driven out when breath is blown into the saliva trap 6, the exhausting gases/vapours leaving the measuring chamber 3 at the open, trumpet-shaped, widened end, through the radiation inlet. Owing to its small volume the measuring chamber 3 will be filled with breath in a very short time. The beam of radiation is focused by the condenser lens 7 and is concentrated onto the surface of a detector 8.

Figure 2:
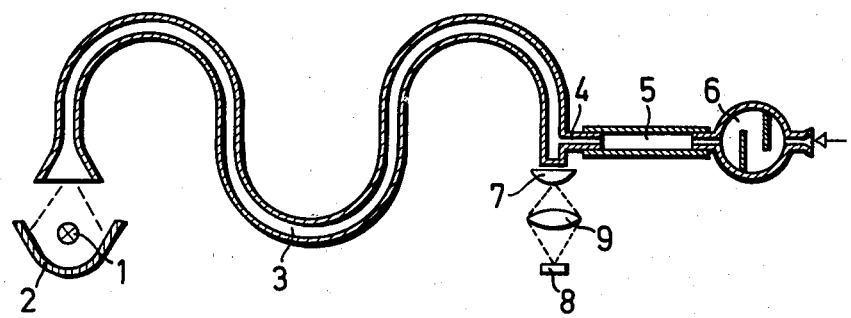

With the embodiment shown in FIG. 2 the measuring chamber is coiled several times in a serpentine manner. The optical equipment is the same as in the embodiment of FIG. 1. An additional lens 9, also transparent to the wavelengths used projects the radiation onto the surface of the detector 8.

Figure 3:
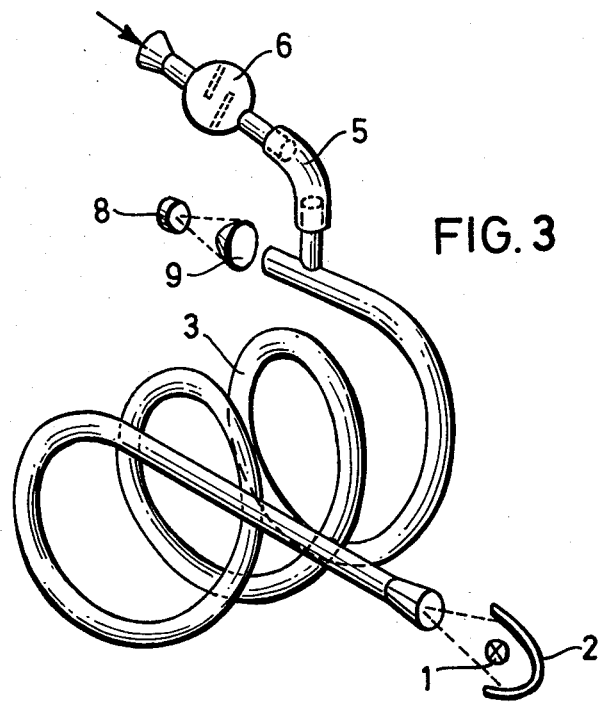
Figure 4:
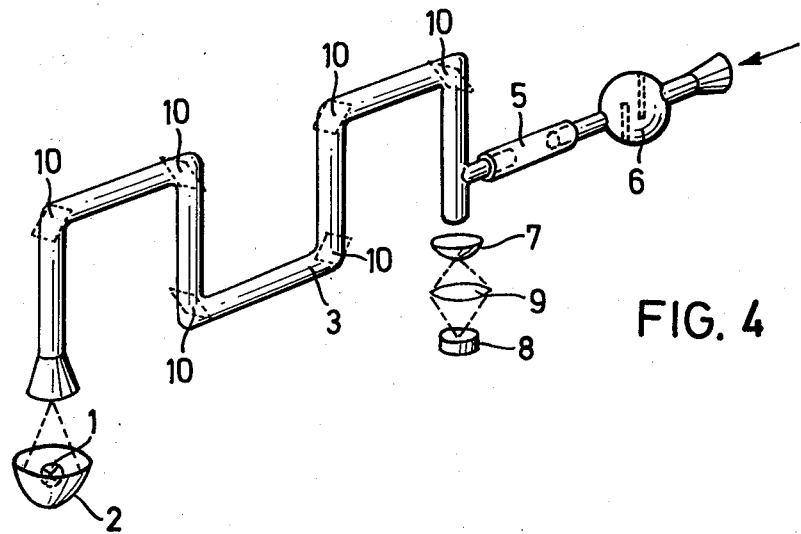

The embodiments shown in FIGS. 3 and 4 are basically similar to the embodiment shown in FIG. 2. In FIG. 3 the tubular measuring chamber 3 is coiled several times in a helix. In FIG. 4 it is coiled in a meandering fashion with definite corners or bends. In the corners between the separate sections of the tube additional plane reflecting surface 10 are arranged. These are arranged to deflect the radiation which impinges thereon through 90°, into the next section of tubing.

Figure 5:
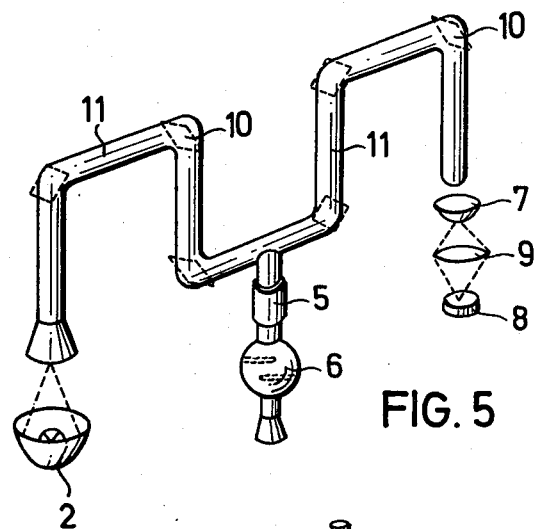

The embodiment shown in FIG. 5 is derived from the embodiment of FIG. 4. Its special feature is the provision of a saliva trap with the blowing-in connection in the centre of a section 11.

Figure 6:
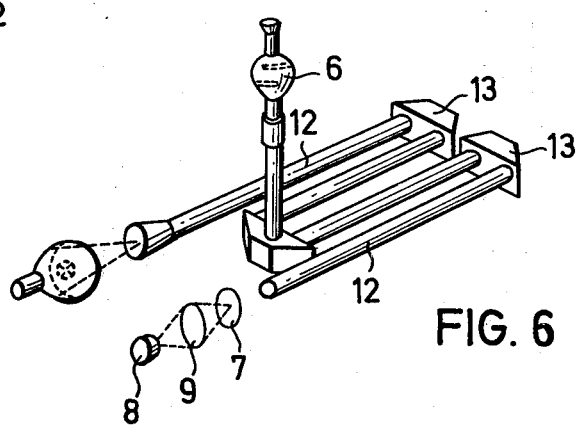

The embodiment shown in FIG. 6 is derived from that shown in FIG. 5. The special feature of this embodiment lies in the fact that the individual sections are different. The measuring chamber 3 consists of longer lengths of tubing 12 extending parallel to each other, with shorter deflecting sections 13 disposed between each two longer lengths 12.

Figure 7:
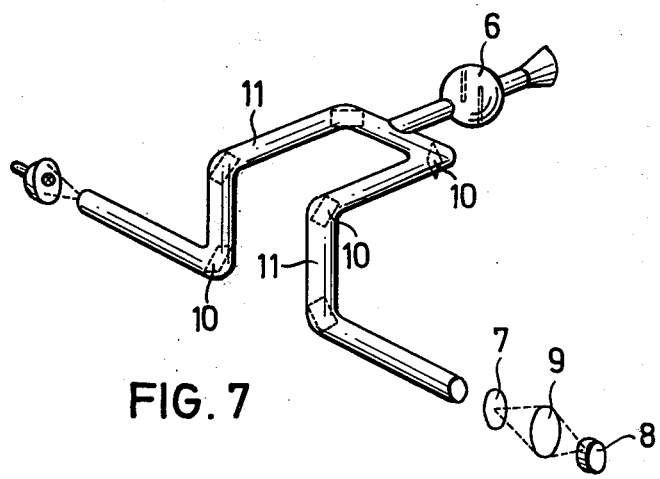

The embodiment shown in FIG. 7 is also derived from that of FIG. 5. Here the individual sections 11 lie in different planes which extend at angles of 90° to each other.

The forms of construction employed in the different embodiments, and especially those of FIGS. 4 to 7, can be intermixed in many ways. For example, in the construction forms shown in FIGS. 6 and 7, the blowing-in connection and the saliva trap can also be arranged at one end of the measuring chamber, as in FIG. 4.

I claim:

1. Apparatus for measuring the concentration of gases by radiation absorption comprising:
a source of infra red radiation;
a detector of infra red radiation;
a plurality of straight tube lengths each having fluid impervious side walls the inner surfaces of which are highly reflective of infra red radiation, a first end of a first of said tube lengths being located adjacent said source to receive infra red radiation therefrom, a first end of a second of said tube lengths being located adjacent said detector to direct infra red radiation thereto;
a plurality of connectors connecting the remaining ones of said plurality of tube lengths in sequence between the second end of said first tube length and the second end of said second tube length, each tube length being in angled relation to the adjacent tube lengths and each connector including infra red radiation reflecting means for directing radiation between successive tube lengths; and
gas inlet means connected to one of said tube lengths intermediate said first end of said first tube length and said first end of said second tube length.

2. The apparatus of claim 1 wherein said tube lengths are connected in right angle radiation to one another.

3. The apparatus of claim 1 wherein each said connector comprises a curved tube section having a planar infra red reflective surface within said connector subtending the angle between adjacent tube sections.

4. The apparatus of 1 wherein certain of said tube lengths lie in different planes.

5. The apparatus of claim 1, 2, 3 or 4 wherein said gas inlet means is located substantially midway between said first ends of said first and second tube lengths.

6. The apparatus of claim 5 wherein said gas inlet means includes a mouthpiece for receiving breath and a saliva trap between said mouthpiece and the connection of said gas inlet means and said tube length.

* * * * *

UNITED STATES PATENT AND TRADEMARK OFFICE
CERTIFICATE OF CORRECTION

PATENT NO. : 4,228,352
DATED : October 14, 1980
INVENTOR(S) : Werner Adrian

It is certified that error appears in the above-identified patent and that said Letters Patent are hereby corrected as shown below:

In the abstract, line 3, for "of" second occurrence read -- by --
In claim 2, col. 6, line 7, for "radiation" read
-- relation --

Signed and Sealed this

Fourteenth Day of July 1981

[SEAL]

Attest:

Attesting Officer

GERALD J. MOSSINGHOFF

Commissioner of Patents and Trademarks